(12) United States Patent
Higashiyama et al.

(10) Patent No.: US 11,167,031 B2
(45) Date of Patent: *Nov. 9, 2021

(54) ADDITIVE COMPOSITION FOR ORALLY DISINTEGRATING TABLET

(71) Applicant: SAWAI PHARMACEUTICAL CO., LTD., Osaka (JP)

(72) Inventors: Yoichi Higashiyama, Osaka (JP); Wataru Izui, Osaka (JP); Ayako Harada, Osaka (JP); Satoru Ogihara, Osaka (JP); Kenji Nozawa, Osaka (JP); Hiroaki Kikuoka, Osaka (JP)

(73) Assignee: SAWAI PHARMACEUTICAL Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/294,114

(22) Filed: Mar. 6, 2019

(65) Prior Publication Data

US 2019/0201529 A1    Jul. 4, 2019

Related U.S. Application Data

(63) Continuation of application No. PCT/JP2017/031863, filed on Sep. 5, 2017.

(30) Foreign Application Priority Data

Sep. 6, 2016    (JP) .............................. JP2016-173470

(51) Int. Cl.
| | | |
|---|---|---|
| *A61K 47/10* | (2017.01) | |
| *A61K 47/38* | (2006.01) | |
| *A61K 47/32* | (2006.01) | |
| *A61K 9/20* | (2006.01) | |
| *A61K 9/00* | (2006.01) | |

(52) U.S. Cl.
CPC ............ *A61K 47/10* (2013.01); *A61K 9/0056* (2013.01); *A61K 9/20* (2013.01); *A61K 9/2018* (2013.01); *A61K 9/2027* (2013.01); *A61K 9/2054* (2013.01); *A61K 9/2095* (2013.01); *A61K 47/32* (2013.01); *A61K 47/38* (2013.01)

(58) Field of Classification Search
CPC ...... A61K 9/0056; A61K 9/20; A61K 9/2018; A61K 9/2027; A61K 9/2054; A61K 9/2095; A61K 47/10; A61K 47/32; A61K 47/38

See application file for complete search history.

(56) References Cited

U.S. PATENT DOCUMENTS

| | | | |
|---|---|---|---|
| 6,154,316 | A | 11/2000 | Fukui et al. |
| 2005/0016670 | A1 | 1/2005 | Kanbara et al. |
| 2007/0275058 | A1 | 11/2007 | Tanaka et al. |
| 2009/0092672 | A1* | 4/2009 | Venkatesh ............ A61K 9/5005 424/490 |
| 2009/0117182 | A1 | 5/2009 | Akutagawa et al. |
| 2009/0148524 | A1* | 6/2009 | Higuchi ............... A61K 9/0056 424/470 |
| 2010/0187706 | A1 | 7/2010 | Maruyama |
| 2010/0286286 | A1 | 11/2010 | Ikeda et al. |
| 2011/0021643 | A1 | 1/2011 | Endo et al. |
| 2011/0053942 | A1 | 3/2011 | Fujiwara et al. |
| 2012/0237602 | A1 | 9/2012 | Ikeda et al. |
| 2013/0338238 | A1 | 12/2013 | Maruyama et al. |
| 2015/0045452 | A1 | 2/2015 | Hiramura et al. |
| 2015/0328163 | A1* | 11/2015 | Gujjar ................. A61K 9/0056 514/410 |
| 2016/0089338 | A1 | 3/2016 | Kawano et al. |

FOREIGN PATENT DOCUMENTS

| | | |
|---|---|---|
| CN | 102006861 A | 4/2011 |
| CN | 102740893 A | 10/2012 |
| CN | 104367560 A | 2/2015 |
| JP | S57-53100 A | 11/1982 |
| JP | H6-281818 A | 10/1994 |
| JP | 2000-327701 A | 11/2000 |

(Continued)

OTHER PUBLICATIONS

Ashland. "PolyplasdoneTM crospovidone superdisintegrants." Retrieved online Feb. 3, 2020. Retrieved from <URL: https://www.ashland.com/file_source/Ashland/Industries/Pharmaceutical/Links/PTR-097_Polyplasdone_crospovidone_as_a_Superdisintegrant.pdf>; pp. 1-4. (Year: 2020).*

Chemopharm. "Comprecel®". Retreived online Feb. 3, 2020; Retreived from <URL: http://www.chemopharma.com/product/comprecel/>; pp. 1-5. (Year: 2020).*

Written Opinion of the International Search Authority dated Nov. 21, 2017 for the PCT application No. PCT/JP2017/031863.

Taiwanese Office Action dated Jun. 29, 2018 for the corresponding Taiwan application No. 106130268, with partial English translation.

International Search Report (PCT/ISA/210) dated Nov. 21, 2017 for the PCT application No. PCT/JP2017/031863, with English translation.

(Continued)

*Primary Examiner* — Doan T Phan
(74) *Attorney, Agent, or Firm* — Hauptman Ham, LLP

(57) ABSTRACT

Provided is a novel additive for an orally disintegrating tablet providing quick disintegrability and tablet hardness to the orally disintegrating tablet, and a producing method therefor. According to an embodiment of the present invention, there is provided an additive for an orally disintegrating tablet characterized by including D-mannitol, low-substituted hydroxypropyl cellulose (however, excluding the low-substituted hydroxypropyl cellulose having a mean particle size of 20 μm or less and a substitution degree of hydroxypropoxy groups of 11%, a mean particle size of 45 μm or less and a substitution degree of hydroxypropoxy groups of 14%, and a mean particle size of 45 μm or less and a substitution degree of hydroxypropoxy groups of 11% and a 90% cumulated particle size of 100 μm or less), crospovidone, and microcrystalline cellulose, wherein the low-substituted hydroxypropyl cellulose and the crospovidone are included in a ratio of 5:4.

8 Claims, 12 Drawing Sheets

(56) References Cited

FOREIGN PATENT DOCUMENTS

| | | | |
|---|---|---|---|
| JP | 2004-250153 | A | 9/2004 |
| JP | 2005-37417 | A | 2/2005 |
| JP | 2007-76106 | A | 3/2007 |
| JP | 2009-515871 | A | 4/2009 |
| JP | 4377964 | B1 | 12/2009 |
| JP | 2010-254756 | A | 11/2010 |
| JP | 2011-2728 | A | 1/2011 |
| JP | 2011-118262 | A | 6/2011 |
| JP | 2011-227336 | A | 11/2011 |
| JP | 2011-257463 | A | 12/2011 |
| JP | 2012-51810 | A | 3/2012 |
| JP | 2012-242607 | A | 12/2012 |
| JP | 2014-15459 | A | 1/2014 |
| JP | 2014-95833 | A | 5/2014 |
| JP | 2014-224911 | A | 12/2014 |
| JP | 5753661 | B2 | 7/2015 |
| WO | 2005/037254 | A1 | 4/2005 |
| WO | 2007/055427 | A1 | 5/2007 |
| WO | 2007/074856 | A1 | 7/2007 |
| WO | 2009/066773 | A1 | 5/2009 |
| WO | 2009/123102 | A1 | 10/2009 |
| WO | 2010/119851 | A1 | 10/2010 |
| WO | 2011068174 | A1 | 6/2011 |
| WO | 2013/146917 | A1 | 10/2013 |
| WO | 2014/185099 | A1 | 11/2014 |
| WO | 2014/189034 | A1 | 11/2014 |
| WO | 2015/053227 | A1 | 4/2015 |

OTHER PUBLICATIONS

Mare Nishiura, "Current Status and Formulation Design of Orally Disintegraitng Tablets in Hospital Preparations", Journal of Pharmaceutical Science and Technology, Japan, 2012, vol. 72, No. 1, p. 30-34, with partial English machine translation.
Japanese Office Action dated Aug. 27, 2019 for the corresponding Japanese patent application No. 2018-538405, with partial English machine translation.
International Search Report for corresponding international application PCT/KR2017/025759 dated Sep. 26, 2017.
English translation of Written Opinion of the International Search Authority dated Nov. 21, 2017 for the corresponding PCT application No. PCT/JP2017/031863.
Examination Report issued for corresponding Indian Patent Application No. 201917011160 dated Nov. 2, 2020.
Notice of Hearing issued for corresponding Indian Patent Application No. 201917011160 dated Mar. 11, 2021.
Written Opinion of the International Search Authority dated Sep. 12, 2017 for the PCT application No. PCT/JP2017/026762 (correspond to co-pending U.S. Appl. No. 16/258,235).
Office Action dated Nov. 20, 2018 for Japanese patent application No. 2018-529889 (correspond to co-pending U.S. Appl. No. 16/258,235).
Kalyan K. Saripella et al., "A Quality by Experimental Design Approach to Assess the Effect of Formulation and Process Variables on the Extrusion and Spheronization of Drug-Loaded Pellets Containing Polyplasdone XL-10" AAPS PharmSciTech, Apr. 2016, 17(2), p. 368-379.
International Search Report (PCT/ISA/210) dated Sep. 12, 2017 for the PCT application No. PCT/JP2017/026762 (correspond to co-pending U.S. Appl. No. 16/258,235).
English translation of Written Opinion of the International Search Authority dated Sep. 12, 2017 for the corresponding PCT application No. PCT/JP2017/026762 (correspond to co-pending U.S. Appl. No. 16/258,235).
English machine translation of Office Action dated Nov. 20, 2018 for the corresponding Japanese patent application No. 2018-529889 (correspond to co-pending U.S. Appl. No. 16/258,235).
Office Action dated May 21, 2019 for the corresponding Japanese patent application No. 2018-529889 (correspond to co-pending U.S. Appl. No. 16/258,235), with partial English machine translation.
"F-MELT—Fast Melt Tablets Made Easy!" accessed from http://www.fujichemical.co.jp/english/medical/medicine/f-melt/f-melt_brochure.pdf.
Japanese Pharmacopeia 16th Edition excerpt, pp. 937-938.
Shin-Etsu L-H PC, accessed from https://www.metolose.jp/en/pharmaceutical/l-hpc.html.
Examination Report issued for corresponding Indian Patent Application No. 201917007396 dated Nov. 3, 2020 (correspond to co-pending U.S. Appl. No. 16/258,235).
Office Action issued for co-pending U.S. Appl. No. 16/258,235 dated Jan. 6, 2021.

* cited by examiner

FIG. 1

| D-mannitol | | Reference Example 1 | Comparative Example 1 | Comparative Example 2 |
|---|---|---|---|---|
| | | Mannit P | PEARLITOL 100SD | Mannit Q |
| Tableting pressures 6kN | Hardness (N) | 36 | 88 | 90 |
| | Oral disintegration times (sec) | 22 | 22 | 20 |
| Tableting pressures 9kN | Hardness (N) | 62 | 151 | 149 |
| | Oral disintegration times (sec) | 22 | 29 | 26 |
| Tableting pressures 12kN | Hardness (N) | 82 | 195 | 195 |
| | Oral disintegration times (sec) | 20 | 50 | 43 |

FIG. 2

| | | Reference Example 2 | Reference Example 3 | Reference Example 4 | Comparative Example 3 | Comparative Example 4 |
|---|---|---|---|---|---|---|
| Tableting pressures 6kN | Hardness (N) | 30 | 41 | 33 | 49 | 41 |
| | Oral disintegration times (sec) | 12 | 14 | 14 | 17 | 16 |
| Tableting pressures 9kN | Hardness (N) | 56 | 64 | 50 | 77 | 61 |
| | Oral disintegration times (sec) | 10 | 19 | 15 | 23 | 24 |
| Tableting pressures 12kN | Hardness (N) | 75 | 84 | 66 | 98 | 78 |
| | Oral disintegration times (sec) | 16 | 28 | 23 | 40 | 36 |

FIG. 3

| | | Reference Example 5 | Reference Example 6 | Comparative Example 5 | Comparative Example 6 | Reference Example 7 | Reference Example 8 | Comparative Example 7 |
|---|---|---|---|---|---|---|---|---|
| Microcrystalline cellulose | | PH-101 | UF-711 | KG-1000 | KG-802 | PH-101 | PH-101 | PH-101 |
| Crospovidone | | CL-F | CL-F | CL-F | CL-F | CL-SF | CL-M | CL |
| Tableting pressures 6kN | Hardness (N) | 27 | 28 | | | 33 | 32 | 26 |
| | Oral disintegration times (sec) | 9 | 9 | | | 12 | 11 | 10 |
| Tableting pressures 9kN | Hardness (N) | 49 | 49 | 65 | 57 | 60 | 57 | 42 |
| | Oral disintegration times (sec) | 11 | 9 | 11 | 9 | 13 | 12 | 11 |
| Tableting pressures 12kN | Hardness (N) | 68 | 67 | 88 | 70 | 79 | 78 | 58 |
| | Oral disintegration times (sec) | 11 | 11 | 14 | 12 | 13 | 15 | 11 |

FIG. 4

|  |  | Reference Example 5 | Comparative Example 8 | Comparative Example 9 |
|---|---|---|---|---|
| Tableting pressures 6kN | Hardness (N) | 27 | | 15 |
| | Oral disintegration times (sec) | 9 | | 8 |
| Tableting pressures 9kN | Hardness (N) | 49 | | 24 |
| | Oral disintegration times (sec) | 11 | | 10 |
| Tableting pressures 12kN | Hardness (N) | 68 | | 27 |
| | Oral disintegration times (sec) | 11 | | 11 |

FIG. 5

| Disintegrant | | Reference Example 5<br>Crospovidone CL-F | Comparative Example 10<br>Partly pregelatinized starch PCS | Comparative Example 11<br>Carmellose NS-300 |
|---|---|---|---|---|
| Tableting pressures 6kN | Hardness (N) | 27 | 25 | |
| | Oral disintegration times (sec) | 9 | 11 | |
| Tableting pressures 9kN | Hardness (N) | 49 | 42 | 42 |
| | Oral disintegration times (sec) | 11 | 15 | 12 |
| Tableting pressures 12kN | Hardness (N) | 68 | 55 | 57 |
| | Oral disintegration times (sec) | 11 | 20 | 18 |

FIG. 6

| L-HPC | | Comparative Example 12 | Comparative Example 13 |
|---|---|---|---|
| | | NBD-020 | NBD-022 |
| Tableting pressures 6kN | Hardness (N) | 40 | 25 |
| | Oral disintegration times (sec) | 33 | 11 |
| Tableting pressures 9kN | Hardness (N) | 60 | 35 |
| | Oral disintegration times (sec) | 44 | 13 |
| Tableting pressures 12kN | Hardness (N) | 56 | 30 |
| | Oral disintegration times (sec) | 59 | 15 |

FIG. 7

| Premixed additive | | Reference Example 8 | Comparative Example 14 | Comparative Example 15 | Comparative Example 16 | Comparative Example 17 |
|---|---|---|---|---|---|---|
| | | Present application | GRANFILLER-D | Pharmaburst | Smart EX | Partech ODT |
| Tableting pressures 6kN | Hardness (N) | 32 | 33 | 34 | 56 | 40 |
| | Oral disintegration times (sec) | 11 | 10 | 11 | 27 | 60 |
| Tableting pressures 9kN | Hardness (N) | 57 | 53 | 51 | 78 | 107 |
| | Oral disintegration times (sec) | 12 | 11 | 13 | 42 | 88 |
| Tableting pressures 12kN | Hardness (N) | 78 | 63 | 64 | 111 | 183 |
| | Oral disintegration times (sec) | 15 | 11 | 15 | 82 | 105 |

FIG. 8

| Premixed additive | | Reference Example 5 | Comparative Example 14 | Comparative Example 15 |
|---|---|---|---|---|
| | | Present application | GRANFILLER-D | Pharmaburst |
| Initial | Thicknesses (mm) | 3.71 | 3.78 | 4.18 |
| | Hardness (N) | 49 | 53 | 51 |
| 25°C75%RH 1W | Thicknesses (mm) (variations mm) | 3.86 (+0.15) | 4.2 (+0.42) | 5.5 (+1.32) |
| | Hardness (N) | 38 | 25 | 0 |
| | Decrease ratio in hardness (%) | 22.4 | 52.8 | 100.0 |

FIG. 9

| | | Example 1 | Example 2 | Example 3 | Example 4 | Example 5 |
|---|---|---|---|---|---|---|
| Tableting pressures 6kN | Hardness (N) | 32 | 33 | 31 | 32 | 32 |
| | Oral disintegration times (sec) | 10 | 10 | 8 | 8 | 9 |
| Tableting pressures 9kN | Hardness (N) | 53 | 59 | 52 | 52 | 54 |
| | Oral disintegration times (sec) | 10 | 11 | 9 | 10 | 10 |
| Tableting pressures 12kN | Hardness (N) | 78 | 79 | 70 | 73 | 75 |
| | Oral disintegration times (sec) | 14 | 12 | 11 | 11 | 10 |
| | | Comparative Example 18 | Comparative Example 19 | Comparative Example 20 | Comparative Example 21 | Comparative Example 22 |
| Tableting pressures 6kN | Hardness (N) | 22 | 27 | 28 | 26 | 27 |
| | Oral disintegration times (sec) | 15 | 15 | 16 | 17 | 15 |
| Tableting pressures 9kN | Hardness (N) | 35 | 43 | 46 | 45 | 41 |
| | Oral disintegration times (sec) | 5 | 18 | 16 | 18 | 18 |
| Tableting pressures 12kN | Hardness (N) | 51 | 59 | 64 | 61 | 58 |
| | Oral disintegration times (sec) | 19 | 17 | 18 | 20 | 20 |

FIG. 10

| | Example 1 | Example 2 | Example 3 | Example 4 | Example 5 |
|---|---|---|---|---|---|
| Wight (mg) | +2.7 | +4.3 | +2.6 | +3.6 | +3.8 |
| Thicknesses (mm) | +0.14 | +0.16 | +0.13 | +0.16 | +0.19 |
| Hardness (N) | -15 | -16 | -16 | -18 | -21 |
| Oral disintegration times (sec) | ±0 | ±0 | +3 | +2 | +1 |

FIG. 11

| | | Example 2 | Example 6 | Example 7 | Example 8 | Example 9 | Example 10 | Example 11 |
|---|---|---|---|---|---|---|---|---|
| Tableting pressures 6kN | Hardness (N) | 33 | 46 | 53 | 61 | 39 | 43 | 56 |
| | Oral disintegration times (sec) | 10 | 10 | 10 | 10 | 8 | 9 | 15 |
| Tableting pressures 9kN | Hardness (N) | 59 | 73 | 82 | 85 | 67 | 72 | 85 |
| | Oral disintegration times (sec) | 11 | 10 | 10 | 13 | 9 | 11 | 15 |
| Tableting pressures 12kN | Hardness (N) | 79 | 91 | 104 | 114 | 84 | 91 | 112 |
| | Oral disintegration times (sec) | 12 | 11 | 13 | 17 | 11 | 11 | 23 |

FIG. 12

|  | Example 2 | Example 7 |
|---|---|---|
| Wight (mg) | +4.3 | +3.4 |
| Thicknesses (mm) | +0.16 | +0.08 |
| Hardness (N) | -16 | -23 |
| Oral disintegration times (sec) | 0 | -2 |

ADDITIVE COMPOSITION FOR ORALLY DISINTEGRATING TABLET

CROSS REFERENCE TO RELATED APPLICATIONS

This application is based upon and claims the benefit of priority from the prior Japanese Patent Application No. 2016-173470, filed on Sep. 6, 2016, and PCT Application No. PCT/JP2017/031863, filed on Sep. 5, 2017, the entire contents of which are incorporated herein by reference.

FIELD

The present invention relates to an additive for an orally disintegrating tablet and a method for producing the additive for an orally disintegrating tablet. In particular, the present invention relates to an additive for an orally disintegrating tablet providing a quick disintegrating property and tablet hardness to an orally disintegrating tablet by adding the additive and a method for producing the additive for the orally disintegrating tablet.

BACKGROUND

An orally disintegrating tablet is a solid preparation quickly disintegrating intraorally and capable of being taken with intraoral saliva or with a small amount of water. Therefore, needs for an orally disintegrating tablet easy for a patient to take are growing. It is desired that the orally disintegrating tablet quickly disintegrate intraorally in about 30 seconds or less only with intraoral saliva or with a small amount of water.

On the other hand, the orally disintegrating tablet is required to have a certain hardness for the sake of manufacturability of the orally disintegrating tablet and for ease of handling by a patient. Therefore, the disintegration time and the hardness of the orally disintegrating tablet need to be adjusted to within a predetermined range.

For adjusting the disintegration time and the hardness of the orally disintegrating tablet, it is necessary to examine a kind or content of an additive to be added to the orally disintegrating tablet variously. Since enormous combinations are assumed in such an examination of the kind and content of an additive, huge labor and cost are required. Therefore, a premix additive in which the composition was examined preliminarily is proposed.

For example, Japanese Patent Application Laid-Open No. 2014-015459 describes a producing method for composite granules including at least a granulation step of granulating a second sugar or sugar alcohol while adding an aqueous dispersion containing low-substituted hydroxypropyl cellulose having a hydroxypropoxy group substitution degree of 5 to 16 mass %, polyvinyl alcohol, a first sugar or sugar alcohol, and water. Japanese Patent Application Laid-Open No. 2014-015459 discloses a base for an orally disintegrating tablet using a method for producing a tablet described in Japanese Patent No. 5753661.

International Publication No. 2013/146917 describes a producing method for a disintegrating particle composition including three ingredients of a first disintegrant ingredient comprising acid type carboxymethyl cellulose; a second disintegrant ingredient including at least one ingredient selected from crospovidone, croscarmellose sodium, sodium carboxymethyl starch, low-substituted hydroxypropyl cellulose, and carboxymethyl cellulose calcium; and an excipient, the producing method including a first wet-type granulating step using any two ingredients of the three ingredients and a second wet-type granulating step using the granules obtained by the first wet-type granulating step and the remaining one ingredient of the three ingredients, and further describes the producing method including microcrystalline cellulose as a fourth ingredient, and including a third step of mixing microcrystalline cellulose into the granules obtained by the second wet-type granulating step.

The base for an orally disintegrating tablet in Japanese Patent Application Laid-Open No. 2014-015459 takes a long oral disintegration time and is therefore required to have more quick disintegrability. Further, the disintegrating particle composition in International Publication No. 2013/146917 has the problem that, a thickness of the orally disintegrating tablet increases significantly and hardness thereof lowers significantly when it is stored under a humidified condition.

SUMMARY

One object of the present invention is to provide a novel additive for an orally disintegrating tablet providing quick disintegrability and tablet hardness to the orally disintegrating tablet, and a producing method therefor.

According to an embodiment of the present invention, there is provided an additive for an orally disintegrating tablet characterized by including D-mannitol, low-substituted hydroxypropyl cellulose (however, excluding the low-substituted hydroxypropyl cellulose having a mean particle size of 20 µm or less and a substitution degree of hydroxypropoxy groups of 11%, a mean particle size of 45 µm or less and a substitution degree of hydroxypropoxy groups of 14%, and a mean particle size of 45 µm or less and a substitution degree of hydroxypropoxy groups of 11% and a 90% cumulated particle size of 100 µm or less), crospovidone, and microcrystalline cellulose, wherein the low-substituted hydroxypropyl cellulose and the crospovidone are included in a ratio of 5:4.

In the additive for an orally disintegrating tablet, the D-mannitol may have a mean particle size of 50 µm or less.

In the additive for an orally disintegrating tablet, the crospovidone may have a mean particle size of 100 µm or less.

In the additive for an orally disintegrating tablet, the microcrystalline cellulose may have a bulk density of 0.22 $g/cm^3$ or more.

Further, according to an embodiment of the present invention, there is provided an orally disintegrating tablet characterized by including the additive for an orally disintegrating tablet according to any one of the above-described embodiments, and a pharmaceutical active ingredient.

Further, according to one embodiment of the present invention, there is provided a producing method for an additive for an orally disintegrating tablet characterized by including using water as granulation liquid, or preparing dispersion liquid by dispersing in water at least one additive selected from a group consisting of low-substituted hydroxypropyl cellulose (however, excluding the low-substituted hydroxypropyl cellulose having a mean particle size of 20 µm or less and a substitution degree of hydroxypropoxy groups of 11%, a mean particle size of 45 µm or less and a substitution degree of hydroxypropoxy groups of 14%, and a mean particle size is 45 µm or less and a substitution degree of hydroxypropoxy groups of 11% and a 90% cumulated particle size of 100 µm or less), D-mannitol, crospovidone and microcrystalline cellulose; performing granulation while spraying the granulation liquid to a mixture including all of the additives excluding the additive contained in the granulation liquid; and blending the low-substituted hydroxypropyl cellulose and the crospovidone in a ratio of 5:4.

In the producing method for an additive for an orally disintegrating tablet, the D-mannitol may have a mean particle size of 50 µm or less.

In the producing method for an additive for an orally disintegrating tablet, the crospovidone may have a mean particle size of 100 µm or less.

In the producing method for an additive for an orally disintegrating tablet, the microcrystalline cellulose may have a bulk density of 0.22 g/cm$^3$ or more.

BRIEF DESCRIPTION OF DRAWINGS

FIG. 1 shows measurement results of hardness and oral disintegration time at each tableting pressure of an orally disintegrating tablet according to a reference example.

FIG. 2 shows measurement results of hardness and oral disintegration time at each tableting pressure of orally disintegrating tablets according to reference examples.

FIG. 3 shows measurement results of hardness and oral disintegration time at each tableting pressure of orally disintegrating tablets according to reference examples.

FIG. 4 shows measurement results of hardness and oral disintegration time at each tableting pressure of orally disintegrating tablets according to a reference example.

FIG. 5 shows measurement results of hardness and oral disintegration time at each tableting pressure of an orally disintegrating tablet according to a reference example.

FIG. 6 shows measurement results of hardness and oral disintegration time at each tableting pressure of orally disintegrating tablets of comparative examples.

FIG. 7 shows measurement results of hardness and oral disintegration time at each tableting pressure of orally disintegrating tablet according to a reference example.

FIG. 8 shows evaluation results of variations in thickness and hardness of an orally disintegrating tablet according to the reference example before and after storage of the orally disintegrating tablet.

FIG. 9 shows measurement results of hardness and oral disintegration time at each tableting pressure of orally disintegrating tablets according to one example of the present invention.

FIG. 10 shows evaluation results of variations in weight, thickness, hardness and disintegration time of orally disintegrating tablets according to one example of the present invention before and after storage of the orally disintegrating tablets.

FIG. 11 shows measurement results of hardness and oral disintegration time at each tableting pressure of orally disintegrating tablets according to one example of the present invention.

FIG. 12 shows evaluation results of variations in weight, thickness, hardness, and disintegration time of orally disintegrating tablets according to one example of the present invention before and after storage of the orally disintegrating tablets.

DESCRIPTION OF EMBODIMENTS

An additive for an orally disintegrating tablet and a producing method thereof according to the present invention are described below. However, the additive for an orally disintegrating tablet and the producing method thereof according to the present invention should not be construed as being limited to contents of embodiments and examples described below.

An additive for an orally disintegrating tablet according to the present invention contains D-mannitol, low-substituted hydroxypropyl cellulose, crospovidone, and microcrystalline cellulose, and contains the low-substituted hydro-propyl cellulose (also called L-HPC hereinafter) and the crospovidone in a ratio of 5:4 in one embodiment. The present inventors are first persons to find a novel additive for an orally disintegrating tablet containing the L-HPC and the crospovidone in the ratio of 5:4, thereby providing quick disintegrability and tablet hardness to an orally disintegrating tablet.

In the additive for an orally disintegrating tablet according to the present invention, as the L-HPC, a low-substituted hydroxypropyl cellulose having a mean particle size of 20 µm or less and a substitution degree of hydroxypropoxy groups of 11%, a mean particle size of 45 µm or less and a substitution degree of hydroxypropoxy groups of 14%, and a mean particle size of 45 µm or less, a substitution degree of hydroxypropoxy groups of 11% and a 90% cumulated particle size of 100 µm or less is excepted. Here, a measuring method for a substitution degree of hydroxypropoxy group of the low-substituted hydroxypropyl cellulose is based upon Japanese Pharmacopoeia 16th Edition. If the additive contains the L-HPC having a mean particle size of 20 µm or less and a substitution degree of hydroxypropoxy groups of 11%, a mean particle size of 45 µm or less and a substitution degree of hydroxypropoxy groups of 14%, and a mean particle size of 45 µm or less, a substitution degree of hydroxypropoxy groups of 11% and a 90% cumulated particle size of 100 µm or less, the oral disintegration time is prolonged, which is not desired. It should be noted that the mean particle size of the L-HPC is determined by a laser diffraction method widely known to those skilled in the art.

It is preferred that the low-substituted hydroxypropyl cellulose contained in the additive for an orally disintegrating tablet according to one embodiment of the present invention have the mean particle size of 45 µm or more and the substitution degree of hydroxypropoxy groups of 11% or less.

Such an L-HPC is selected from, for example, a group consisting of LH-11, LH-21, LH-22, LH-B1 and NBD-022 produced by Shin-Etsu Chemical Co., Ltd., but is not limited to these. Physical properties of the low-substituted hydroxypropyl cellulose are shown in Table 1. Particularly, since the NBD-022 can obtain a quick oral disintegration time of 20 seconds or less while maintaining hardness of the orally disintegrating tablet, the NBD-022 is preferred. It is to be noted that, since the LH-31, the NBD-021 and the NBD-020 were used as comparative examples described later, the physical properties thereof are shown as a reference.

TABLE 1

|  | Particle appearance | Hydroxy-propoxy group (%) | Mean particle size (µm) | 90% cumulated particle size (µm) |
| --- | --- | --- | --- | --- |
| LH-11 | Most fibrous | 11 | 55 | 175 |
| LH-21 | Moderately fibrous | 11 | 45 | 135 |
| LH-22 | Moderately fibrous | 8 | 45 | 135 |
| LH-B1 | Non fibrous | 11 | 55 | 125 |
| NBD-022 | Short fiber | 8 | 45 | 100 |

TABLE 1-continued

|  | Particle appearance | Hydroxy-propoxy group (%) | Mean particle size (μm) | 90% cumulated particle size (μm) |
|---|---|---|---|---|
| LH-31 | Micronized | 11 | 20 | 70 |
| NBD-021 | Short fiber | 11 | 45 | 100 |
| NBD-020 | Short fiber | 14 | 45 | 100 |

The D-mannitol added to the additive for an orally disintegrating tablet according to the present invention is not particularly limited. In one embodiment, it is preferred that the D-mannitol have a mean particle size of 50 μm or less. As the D-mannitol having a mean particle size of 50 μm or less, for example, Mannit P produced by Mitsubishi Shoji Foodtech Co., Ltd. is mentioned, but is not limited to this. It is to be noted that the mean particle size of the D-mannitol is determined by a laser diffraction method widely known to those skilled in the art.

The crospovidone added to the additive for an orally disintegrating tablet according to the present invention preferably has the mean particle size of 100 μm or less, more preferably has a mean particle size 50 μm or less. It is preferred that the crospovidone having a mean particle size of 100 μm or less is used, since it becomes easy to obtain hardness required for the orally disintegrating tablet. It is to be noted that the mean particle size of the crospovidone is determined by a laser diffraction method widely known to those skilled in the art.

In one embodiment, the crospovidone is selected from, for example, the group consisting of Kollidon CL-F, Kollidon CL-SF and Kollidon CL-M produced by BASF Corporation, but is not limited to these. Physical properties of each crospovidone are shown in Table 2. Particularly, the Kollidon CL-M is preferred since it can obtain a quick oral disintegration time while maintaining hardness of the orally disintegrating tablet.

TABLE 2

|  | Swelling pressure (kPa) | Particle size (μm) |
|---|---|---|
| CL | 170 | 110 to 130 |
| CL-F | 30 | 20 to 40 |
| CL-SF | 25 | 10 to 30 |
| CL-M | 70 | 3 to 10 |

In the additive for an orally disintegrating tablet according to the present invention, a content ratio of the L-HPC to the crospovidone is 5:4. This ratio provides quick disintegrability and hardness, and improves manufacturability in fluidized bed granulation described later.

It is preferred that the microcrystalline cellulose added to the additive for an orally disintegrating tablet according to the present invention have a bulk density of 0.22 g/cm$^3$ or more. Since the microcrystalline cellulose having a bulk density less than 0.22 g/cm$^3$ may bring about sticking occur under a low tableting pressure condition, the microcrystalline cellulose having a bulk density of 0.22 g/cm$^3$ or more is preferred. It is to be noted that the bulk density of the microcrystalline cellulose is determined by a measuring method for a bulk density described in the microcrystalline Cellulose section of Japanese Pharmacopoeia 16th Edition.

In one embodiment, the microcrystalline cellulose is selected from, for example, the group consisting of UF-702, UF-711, PH-101, PH-101D, PH-102, PH-200, PH-301, PH-301D, PH-302 and PH-F20JP produced by Asahi Kasei Corporation, but is not limited to these. Physical properties of each microcrystalline cellulose are shown in Table 3. Particularly, the UF-711 having a mean particle size of 50 μm and a bulk density of 0.22 g/cm$^3$ and the PH-101 having a mean particle size of 50 μm and an bulk density of 0.29 g/cm$^3$ are preferred since they can maintain the hardness of the orally disintegrating tablet without bringing about occurrence of sticking.

TABLE 3

| Grade | Mean particle size (μm) | Bulk density (g/cm$^3$) | Loss on drying (%) | Repose angle (degree) |
|---|---|---|---|---|
| UF-702 | 90 | 0.29 | 2.0-6.0 | 34 |
| UF-711 | 50 | 0.22 | 2.0-6.0 | 42 |
| KG-802 | 50 | 0.21 | 2.0-6.0 | 49 |
| KG-1000 | 50 | 0.12 | 2.0-6.0 | 57 |
| PH-101 | 50 | 0.29 | 2.0-6.0 | 45 |
| PH-101D | 50 | 0.29 | 1.0-3.0 | 45 |
| PH-102 | 90 | 0.3 | 2.0-6.0 | 42 |
| PH-200 | 170 | 0.35 | 2.0-6.0 | 36 |
| PH-301 | 50 | 0.41 | 2.0-6.0 | 41 |
| PH-301D | 50 | 0.41 | 1.0-3.0 | 41 |
| PH-302 | 90 | 0.43 | 2.0-6.0 | 38 |
| PH-F20JP | 20 | 0.23 | 7.0 or less | 60 or more |

The additive for an orally disintegrating tablet according to the present invention can adjust the orally disintegrating tablet to a desired disintegration time and desired hardness by adjusting a grade of each of the above additives and a content of each of the above additives. The additive for an orally disintegrating tablet according to the present invention is a novel additive for an orally disintegrating tablet providing quick disintegrability and tablet hardness to an orally disintegrating tablet.

An orally disintegrating tablet containing the additive for an orally disintegrating tablet according to the present invention and a pharmaceutical active ingredient can be produced. The pharmaceutical active ingredient is not particularly limited, and the orally disintegrating tablet can be produced by using various pharmaceutical active ingredients. The orally disintegrating tablet can be produced by mixing the additive for an orally disintegrating tablet according to the present invention, a pharmaceutical active ingredient and a lubricant and tableting the mixture. The lubricant is not particularly limited, and a known lubricant can be used. As the lubricant, for example, magnesium stearate, stearic acid, calcium stearate, light anhydrous silicic acid, sodium stearyl fumarate, talc, hydrogenated vegetable oil, microcrystalline wax, sucrose fatty acid ester and polyethylene glycol, and the like can be mentioned, but the lubricant is not limited to those.

In the orally disintegrating tablet, for example, a corrigent, flavoring agent, fluidizing agent, antistatic agent, surfactant, humectant, extender, absorbent, dehumidifying agent, antioxidant, preservative (for example, antiseptic agent and the like), buffer agent and the like can be used as the other additives. The orally disintegrating tablet may also be coated with a film.

(Producing Method for Additive for Orally Disintegrating Tablet)

It is preferred that the additive for an orally disintegrating tablet according to the present invention is produced by fluidized bed granulation. Water is used as granulation liquid, or dispersion liquid is prepared as granulation liquid by dispersing at least one additive selected from the group consisting of L-HPC, D-mannitol, crospovidone and microcrystalline cellulose in water, and granulation is performed while spraying the granulation liquid to a mixture containing all the additives excluding the additive contained in the granulation liquid. In the additive for an orally disintegrating tablet according to the present invention, quick disintegrability and tablet hardness can be provided to the orally disintegrating tablet by blending the L-HPC and the crospovidone in a ratio of 5:4.

In the present invention, by blending the L-HPC and the crospovidone in the ratio of 5:4, regardless of whether water is used as the granulation liquid or the dispersion liquid obtained by dispersing any additive of the L-HPC, the D-mannitol, the crospovidone or the microcrystalline cellulose is used, quick disintegrability and tablet hardness can be provided to the orally disintegrating tablet. It is to be noted that it is preferred that the additive for an orally disintegrating tablet according to the present invention be obtained by fluidized bed granulation. Since an agitation kneading method causes a significant reduction in the hardness of the orally disintegrating tablet, it is not preferred that the agitation kneading method be used.

For example, the dispersion liquid is prepared by dispersing at least one additive selected from the group consisting of L-HPC, D-mannitol, crospovidone and microcrystalline cellulose in water (purified water). Performing fluidized bed granulation by dispersing L-HPC into ethanol is not preferred since sticking occurs. A mixture is obtained by mixing the remaining additives which are not used in the dispersion liquid. The additive for an orally disintegrating tablet according to the present invention can be produced by performing fluidized bed granulation while spraying aqueous dispersion to the mixture. Further, it is also possible to use water as the granulation liquid to perform fluidized bed granulation while spraying the water to a mixture obtained by mixing L-HPC, D-mannitol, crospovidone and microcrystalline cellulose. In the additive for an orally disintegrating tablet according to the present invention, it is preferred that the granulated product is sized by a sieve.

(Producing Method for Orally Disintegrating Tablet)

An orally disintegrating tablet can be produced by mixing the additive for an orally disintegrating tablet according to the present invention, a pharmaceutical active ingredient, and a lubricant and tableting the mixture. Further, an orally disintegrating tablet can also be produced by adding and mixing the other additives described above. The orally disintegrating tablet can also be coated with a film by a known method.

As explained above, according to the present invention, a novel additive for an orally disintegrating tablet providing quick disintegrability and tablet hardness to an orally disintegrating tablet, and a producing method therefor can be provided.

EXAMPLE (Examination of Grade of Mannitol)

Influence of a grade of mannitol on an orally disintegrating tablet was examined.

Reference Example 1

As Reference Example 1 of the present invention, an orally disintegrating tablet was produced. Dispersion liquid was prepared by dispersing 55 g of NBD-022 (Shin-Etsu Chemical Co., Ltd.) as the low-substituted hydroxypropyl cellulose into 745 ml of purified water. A fluidized bed granulator (manufactured by POWREX CORP., Model: MP-01) was used to mix 385 g of Mannit P (Mitsubishi Shoji Foodtech Co., Ltd.) as the D-mannitol, 10 g of Kollidon CL-F (BASF Corporation) as the crospovidone, and 50 g of PH-101 (Asahi Kasei Corporation) as the microcrystalline cellulose to obtain a mixture. A fluidized bed granulation was performed while spraying the dispersion liquid to the obtained mixture. An additive for an orally disintegrating tablet of Reference Example 1 was obtained by regulating a grain size of the obtained granulated product with Sieve No. 22. Powder before tableting was obtained by mixing 5 g of magnesium stearate (Taihei Chemical Industrial Co., Ltd.) in the additive for an orally disintegrating tablet of Reference Example 1. The orally disintegrating tablet of Reference Example 1 was obtained by using a tableting machine (VELA5 manufactured by KIKUSUI SEISAKUSHO LTD.) to tablet the powder before tableting so as to obtain a tablet having a weight of 200 mg.

Comparative Example 1

An orally disintegrating tablet of Comparative Example 1 was produced by a method similar to the method used for the orally disintegrating tablet of Reference Example 1, except that, as an additive for an orally disintegrating tablet of Comparative Example 1, the mannitol was changed to PEARLITOL (registered trademark) 100SD (ROQUETTE PHARMA) in the additive for an orally disintegrating tablet of Reference Example 1.

Comparative Example 2

An orally disintegrating tablet of Comparative Example 2 was produced by a method similar to the method used for the orally disintegrating tablet of Reference Example 1, except that, as an additive for an orally disintegrating tablet of Comparative Example 2, the mannitol was changed to Mannit Q (Mitsubishi Shoji Foodtech Co., Ltd.) in the additive for an orally disintegrating tablet of Reference Example 1.

The orally disintegrating tablets of Reference Example 1, and Comparative Examples 1 and 2 were each produced using tableting pressures to 6 kN, 9 kN and 12 kN. Regarding the orally disintegrating tablets of Reference Example 1, and Comparative Examples 1 and 2 tableted using the three tableting pressures, measurement results of hardness and oral disintegration times thereof at the respective tableting pressures are shown in FIG. 1. It is to be noted that the measurement results of FIG. 1 are average values of 5 tablets of each orally disintegrating tablet. FIG. 1 revealed that the orally disintegrating tablet of Reference Example 1 obtained by using Mannit P as the D-mannitol shows excellent disintegrability regardless of the increase in tableting pressure. On the other hand, in the orally disintegrating tablets of Comparative Example 1 using PEARLITOL and Comparative Example 2 using Mannit Q, their oral disintegration times became as slow as 40 seconds or more.

(Examination of Grade of L-HPC)

Influence of a grade of L-HPC on an orally integrating tablet was examined.

Reference Example 2

An orally disintegrating tablet of Reference Example 2 in another lot was produced by a method similar to the method used for the orally disintegrating tablet of Reference Example 1.

Reference Example 3

An orally disintegrating tablet of Comparative Example 3 was produced by a method similar to the method used for the orally disintegrating tablet of Reference Example 1, except that, as an additive for an orally disintegrating tablet of Reference Example 3, the L-HPC was changed to LH-21 (Shin-Etsu Chemical Co.) in the additive for an orally disintegrating tablet of Reference Example 1.

Reference Example 4

An orally disintegrating tablet of Reference Example 4 was produced by a method similar to the method used for the orally disintegrating tablet of Reference Example 1 except that, as an additive for an orally disintegrating tablet of Reference Example 4, the L-HPC was changed to LH-B1 (Shin-Etsu Chemical Co.) in the additive for an orally disintegrating tablet of Reference Example 1.

Comparative Example 3

An orally disintegrating tablet of Comparative Example 3 was produced by a method similar to the method used for the orally disintegrating tablet of Reference Example 1, except that as an additive for an orally disintegrating tablet of Comparative example 3, the L-HPC was changed to LH-31 (Shin-Etsu Chemical Co.) in the additive for an orally disintegrating tablet of Reference Example 1.

Comparative Example 4

An orally disintegrating tablet of Comparative Example 4 was produced by a method similar to the method used for the orally disintegrating tablet of Reference Example 1, except that, as an additive for an orally disintegrating tablet of Comparative example 4, the L-HPC was changed to NBD-021 (Shin-Etsu Chemical Co.) in the additive for an orally disintegrating tablet of Reference Example 1.

The orally disintegrating tablets of Reference Examples 2 to 4 and Comparative Examples 3 and 4 were each produced by setting the tableting pressures of 6 kN, 9 kN and 12 kN. Regarding the orally disintegrating tablets of Reference Examples 2 to 4 and Comparative Examples 3 and 4 tableted using the three tableting pressures, measurement results of hardness and oral disintegration times thereof at the respective tableting pressures are shown in FIG. 2. The results in FIG. 2 revealed that the orally disintegrating tablet of Reference Example 2 using the NBD-022 as L-HPC could obtain hardness according to the tableting pressure and also exhibited most excellent disintegrability. Further, it was revealed that the orally disintegrating tablets of Reference Example 3 using the LH-21 as the L-HPC and Reference Example 4 using the LH-B1 as the L-HPC also obtained hardness according to the tableting pressure and excellent disintegrability. On the other hand, it was revealed that the orally disintegrating tablets of Comparative Example 3 using the LH-31 as the L-HPC and Comparative Example 4 using the NBD-021 as the L-HPC had as slow the oral disintegration times as more than 30 seconds when they were tableted with 12 kN.

It is to be noted that when the dispersion liquid having LH-11 and LH-22 dispersed at the dispersion liquid concentration examined here was used, a spray nozzle in the fluidized bed granulator got clogged. This revealed that, when these grades of L-HPCs were used, it was necessary to change the dispersion liquid concentration. In addition, it was revealed that NBD-020 had too low bulk density and therefore could not be tableted because of underfilling.

(Examination of Grade of Microcrystalline Cellulose)

Influence of a grade of the microcrystalline cellulose on an orally integrating tablet was examined.

Reference Example 5

An orally disintegrating tablet of Reference Example 5 was produced by a method similar to the method used for the orally disintegrating tablet of Reference Example 1, except that, as an additive for an orally disintegrating tablet of Reference Example 5, the D-mannitol was changed to 410 g, the L-HPC to 25 g, and the crospovidone to 15 g in the additive for an orally disintegrating tablet of Reference Example 1.

Reference Example 6

An orally disintegrating tablet of Reference Example 6 was produced by a method similar to the method used for the orally disintegrating tablet of Reference Example 5, except that, As an additive for an orally disintegrating tablet of Reference Example 6, the microcrystalline cellulose is changed to UF-711 (Asahi Kasei Corporation) in the additive for an orally disintegrating tablet of Reference Example 5.

Comparative Example 5

An orally disintegrating tablet of Comparative Example 5 was produced by a method similar to the method used for the orally disintegrating tablet of Reference Example 5, except that, as an additive for an orally disintegrating tablet of Comparative Example 5, the microcrystalline cellulose was changed to KG-1000 (Asahi Kasei Corporation) in the additive for an orally disintegrating tablet of Reference Example 5.

Comparative Example 6

An orally disintegrating tablet of Comparative Example 6 was produced by a method similar to the method used for the orally disintegrating tablet of Reference Example 5, except that, as an additive for an orally disintegrating tablet of Comparative Example 6, the microcrystalline cellulose was changed to KG-802 (Asahi Kasei Corporation) in the additive for an orally disintegrating tablet of Reference Example 5.

The orally disintegrating tablets of Reference Examples 5 and 6 and Comparative Examples 5 and 6 were each produced using the tableting pressures of 6 kN, 9 kN and 12 kN. Regarding the orally disintegrating tablets of Reference Examples 5 and 6 and Comparative Examples 5 and 6 tableted using the three tableting pressures, measurement results of hardness and oral disintegration times thereof at the respective tableting pressures are shown in FIG. 3. It is to be noted that the measurement results of FIG. 3 are average values of 5 tablets of each orally disintegrating tablet. The results in FIG. 3 revealed that the orally disintegrating tablet of Reference Example 5 using PH-101 as the microcrystalline cellulose and the orally disintegrating tablet of Reference Example 6 using UF-711 as the microcrystalline cellulose could obtain sufficient hardness. However, it was revealed that the orally disintegrating tablets of Comparative Example 5 using KG-1000 as the microcrystalline cellulose and Comparative Example 6 using KG-802 as the microcrystalline cellulose brought about sticking and poor fluidity of powder before tableting when tableting was performed at 6 kN.

(Examination of Grade of Crospovidone)

Influence of a grade of crospovidone on an orally integrating tablet was examined.

Reference Example 7

An orally disintegrating tablet of Comparative Example 7 was produced by a method similar to the method used for the orally disintegrating tablet of Reference Example 5, except that, as an additive for an orally disintegrating tablet of Reference Example 7, the crospovidone was changed to Kollidon CL-SF (BASF Corporation) in the additive for an orally disintegrating tablet of Reference Example 5.

Reference Example 8

An orally disintegrating tablet of Comparative Example 8 was produced by a method similar to the method used for the orally disintegrating tablet of Reference Example 5, except that, as an additive for an orally disintegrating tablet of Reference Example 8, the crospovidone was changed to Kollidon CL-M (BASF Corporation) in the additive for an orally disintegrating tablet of Reference Example 5.

Comparative Example 7

An orally disintegrating tablet of Comparative Example 7 was produced by a method similar to the method used for the orally disintegrating tablet of Reference Example 5, except that, as an additive for an orally disintegrating tablet of Reference Example 7, the crospovidone was changed to Kollidon CL (BASF Corporation) in the additive for an orally disintegrating tablet of Reference Example 5.

The orally disintegrating tablets of Reference Examples 5, 7 and 8 and Comparative Example 7 were each produced using the tableting pressures to 6 kN, 9 kN and 12 kN, respectively. Regarding the orally disintegrating tablets of Reference Examples 5, 7 and 8 and Comparative Example 7 tableted using the three tableting pressures, measurement results of hardness and oral disintegration times thereof at the respective tableting pressures are shown in FIG. 3. It is to be noted that the measurement results of FIG. 3 are average values of 5 tablets of each orally disintegrating tablet. The result in FIG. 3 revealed that the orally disintegrating tablets of Reference Example 5 using Kollidon CL-F as the crospovidone, Reference Example 7 using Kollidon CL-SF as the crospovidone, and Reference Example 8 using Kollidon CL-M as the crospovidone could obtain sufficient hardness according to the tableting pressure. On the other hand, it was revealed that the orally disintegrating tablet of Comparative Example 7 using Kollidon CL as the crospovidone could not obtain sufficient hardness.

(Comparison of Producing Methods)

Producing methods other than the above-described Examples were examined.

Comparative Example 8

As Comparative Example 8, an orally disintegrating tablet using ethanol partially as a solvent of the dispersion liquid was produced. The dispersion liquid was prepared by dispersing 25 g of NBD-022 (Shin-Etsu Chemical Co., Ltd.) as the L-HPC in 350 mL of mixed liquid of ethanol:purified water=8:2. In a fluidized bed granulator (POWREX CORP., Model: MP-01), a mixture was obtained by mixing 410 g of Mannit P (Mitsubishi Shoji Foodtech Co., Ltd.) as the D-mannitol, 15 g of Kollidon CL-F (BASF Corporation) as the crospovidone and 50 g of PH-101 (Asahi kasei Corporation) as the microcrystalline cellulose. Fluidized bed granulation was performed while spraying the dispersion liquid to the obtained mixture. An additive for an orally disintegrating tablet of Comparative Example 8 was obtained by sizing the obtained granulated product with Sieve No. 22. Powder before tableted was obtained by mixing 5 g of magnesium stearate (Taihei Chemical Industrial Co., Ltd.) into the additive for an orally disintegrating tablet of Comparative Example 8. An orally disintegrating tablet of Comparative Example 8 was obtained by using a tableting machine (VELA5, KIKUSUI SEISAKUSHO LTD.) to tablet the powder before tableting so as to obtain a tablet having a weight of 200 mg.

Comparative Example 9

An additive for an orally disintegrating tablet of Comparative Example 9 was obtained by agitation kneading.

The orally disintegrating tablets of Reference Example 5 and Comparative Examples 8 and 9 were each produced using the tableting pressures of 6 kN, 9 kN and 12 kN. Regarding the orally disintegrating tablets of Reference Example 5 and Comparative Examples 8 and 9 tableted using the three tableting pressures, measurement results of hardness and oral disintegration times thereof at the respective tableting pressures are shown in FIG. 4. The measurement results of FIG. 4 revealed that the orally disintegrating tablet of Reference Example 5 could obtain sufficient hardness according to the tableting pressure. On the other hand, tableting could not be performed with the additive for an orally disintegrating tablet of Comparative Example 8. Further, an orally disintegrating tablet of Comparative Example 9 obtained by the agitation kneading could not obtain sufficient hardness.

(Examination of Disintegrant)

Disintegrants other than the crospovidone were examined.

Comparative Example 10

As Comparative Example 10, dispersion liquid was prepared by dispersing 25 g of NBD-022 (Shin-Etsu Chemical Co., Ltd.) as the L-HPC into 350 ml of purified water. Fluidized bed granulation was performed in a fluidized bed granulator (manufactured by POWREX CORP., Model: MP-01) while spraying the above-described dispersion liquid to a mixture of 410 g of Mannit P (Mitsubishi Shoji Foodtech Co., Ltd.) as the D-mannitol, 15 g of partly pregelatinized starch PCS (Asahi Kasei Corporation) as the disintegrant, and 50 g of PH-101 (Asahi Kasei Corporation) as the microcrystalline cellulose. An additive for an orally disintegrating tablet of Comparative Example 10 was obtained by sizing the obtained granulated product with Sieve No. 22. Powder before tableting was obtained by mixing 5 g of magnesium stearate (Taihei Chemical Industrial Co., Ltd.) into the additive for an orally disintegrating tablet of Comparative Example 10. An orally disintegrating tablet of Comparative Example 10 was obtained by using a tableting machine (VELA5, KIKUSUI SEISAKUSHO LTD.) to tablet the powder before tableted so as to obtain a tablet having a weight of 200 mg.

Comparative Example 11

As Comparative Example 11, dispersion liquid was prepared by dispersing 25 g of NBD-022 (Shin-Etsu Chemical Co., Ltd.) as the L-HPC into 350 ml of purified water. Fluidized bed granulation was performed in a fluidized bed granulator (manufactured by POWREX CORP., Model: MP-01) while spraying the above-described dispersion liquid to mixture of 410 g of Mannit P (Mitsubishi Shoji Foodtech Co., Ltd.) as the D-mannitol, 15 g of carmellose NS-300 (Gotoku Chemical Company Ltd.) as the disintegrant, and 50 g of PH-101 (Asahi Kasei Corporation) as the microcrystalline cellulose. An additive for an orally disintegrating tablet of Comparative Example 11 was obtained by sizing the obtained granulated product with Sieve No. 22. Powder before tableted was obtained by mixing 5 g of magnesium stearate (Taihei Chemical Industrial Co., Ltd.) to the additive for an orally disintegrating tablet of Comparative Example 11. The orally disintegrating tablet of Comparative Example 11 was obtained by using a tableting machine (VELA5 manufactured by KIKUSUI SEISAKUSHO LTD.) to tablet the powder before tableting to obtain a tablet having a weight of 200 mg.

The orally disintegrating tablets of Reference Example 5 and Comparative Examples 10 and 11 were each produced using the tableting pressures to 6 kN, 9 kN and 12 kN. Regarding the orally disintegrating tablets of Reference Example 5 and Comparative Examples 10 and 11 tableted using the three tableting pressures, measurement results of hardness and oral disintegration times thereof at the respective tableting pressures are shown in FIG. 5. The measurement result in FIG. 5, it revealed that the orally disintegrating tablet of Reference Example 5 using crospovidone as the disintegrant could obtain sufficient hardness according to the tableting pressure. On the other hand, in the additive for an orally disintegrating tablet of Comparative Example 10 using partly pregelatinized starch as the disintegrant could not obtain sufficient hardness. Further, the orally disintegrating tablet of Comparative Example 11 using carmellose as the disintegrant brought about sticking.

Comparative Example 12

As Comparative Example 12, an orally disintegrating tablet was produced according to Example 1 of Japanese Patent No. 5753661. Dispersion liquid was prepared by dispersing 25 g of NBD-020 (Shin-Etsu Chemical Co., Ltd.) as the L-HPC into 350 ml of purified water. Fluidized bed granulation was performed in a fluidized bed granulator (manufactured by POWREX CORP., Model: MP-01) while spraying the above-described dispersion liquid to 475 g of Mannit P (Mitsubishi Shoji Foodtech Co., Ltd.) as the D-mannitol. An additive for an orally disintegrating tablet of Comparative Example 12 was obtained by sizing the obtained granulated product with Sieve No. 22. Powder before tableted was obtained by mixing 5 g of magnesium stearate (Taihei Chemical Industrial Co., Ltd.) in the additive for an orally disintegrating tablet of Comparative Example 12. The orally disintegrating tablet of Comparative Example 12 was obtained by using a tableting machine (VELA5 manufactured by KIKUSUI SEISAKUSHO LTD.) to tablet the powder before tableted to obtain a tablet having a weight of 200 mg.

Comparative Example 13

As Comparative Example 13, an orally disintegrating tablet of Comparative Example 13 was produced by a method similar to the method of Comparative Example 12, except that NBD-020 was changed to NBD-022 (Shin-Etsu Chemical Co., Ltd.) as the L-HPC.

The orally disintegrating tablets of Comparative Examples 12 and 13 were each produced using the tableting pressures of 6 kN, 9 kN and 12 kN. Regarding the orally disintegrating tablets of Comparative Examples 12 and 13 tableted using the three tableting pressures, measurement results of hardness and oral disintegration times thereof at the respective tableting pressures are shown in FIG. 6. From the measurement results in FIG. 6, the orally disintegrating tablet of Comparative Example 12 according to Japanese Patent No. 5753661 could not obtain sufficient hardness and quick oral disintegration time. Further, from the result of Comparative Example 13, sufficient hardness could not be obtained by changing the grade of the L-HPC alone.
(Comparison with Conventional Premixed Additive)

An orally disintegrating tablet was produced using a conventional premixed additive and comparison was performed.

Comparative Example 14

An orally disintegrating tablet was produced by using GRANFILLER-D (registered trademark) (Daicel FineChem Ltd.) as an additive for an orally disintegrating tablet of Comparative Example 14. Powder before tableted was obtained by mixing 5 g of magnesium stearate (Taihei Chemical Industrial Co., Ltd.) in 500 g of the additive for an orally disintegrating tablet of Reference Example 14. An orally disintegrating tablet of Comparative Example 14 was obtained by using a tableting machine (VELA5 manufactured by KIKUSUI SEISAKUSHO LTD.) to tablet the powder before tableting to obtain a tablet having a weight of 200 mg.

Comparative Example 15

An orally disintegrating tablet was produced by using Pharmaburst (registered trademark) (SPI Pharma) as an additive for an orally disintegrating tablet of Comparative Example 15. Powder before tableted was obtained by mixing 5 g of magnesium stearate (Taihei Chemical Industrial Co., Ltd.) in 500 g of the additive for an orally disintegrating tablet of Comparative Example 15. An orally disintegrating tablet of Comparative Example 15 was obtained by using a tableting machine (VELA5 manufactured by KIKUSUI SEISAKUSHO LTD.) to tablet the powder before tableting to obtain a tablet having a weight of 200 mg.

Comparative Example 16

An orally disintegrating tablet was produced by using Smart EX (registered trademark) (Freund Corporation) as an additive for an orally disintegrating tablet of Comparative Example 16. Powder before tableted was obtained by mixing 5 g of magnesium stearate (Taihei Chemical Industrial Co., Ltd.) in 500 g of the additive for an orally disintegrating tablet of Comparative Example 16. An orally disintegrating tablet of Comparative Example 16 was obtained by using a tableting machine (VELA5 manufactured by KIKUSUI SEISAKUSHO LTD.) to tablet the powder before tableting to obtain a tablet having a weight of 200 mg.

Comparative Example 17

An orally disintegrating tablet was produced by using Partech (registered trademark) ODT (Merck) as an additive for an orally disintegrating tablet of Comparative Example 17. Powder before tableted was obtained by mixing 5 g of magnesium stearate (Taihei Chemical Industrial Co., Ltd.) in 500 g of the additive for an orally disintegrating tablet of Comparative Example 17. An orally disintegrating tablet of Comparative Example 17 was obtained by using a tableting machine (VELA5 manufactured by KIKUSUI SEISAKUSHO LTD.) to tablet the powder before tableted to obtain a tablet of a weight of 200 mg.

The orally disintegrating tablets of Reference Example 8 and Comparative Examples 14 to 17 were each produced using the tableting pressures of 6 kN, 9 kN and 12 kN. Regarding the orally disintegrating tablets of Reference Example 8 and Comparative Examples 14 to 17 tableted using the three tableting pressures, measurement results of hardness and oral disintegration times thereof at the respective tableting pressures are shown in FIG. 7. From the measurement results in FIG. 7, the orally disintegrating tablet of the Reference Example 8 exhibited sufficient hardness and a quick disintegrability time of 30 seconds or less as compared with the orally disintegrating tablets of Comparative Examples 14 to 17. In addition, the orally disintegrating tablet of Reference Example 8 exhibited sufficient hardness and excellent disintegrability equal to or more than those of the orally disintegrating tablets of Comparative Examples 14 and 15.

(Evaluation of Humidity Resistance)

The orally disintegrating tablets of Reference Example 5 and Comparative Examples 14 and 15 were produced using the tableting pressure of 9 kN. The orally disintegrating tablets of Reference Example 5 and Comparative Examples 14 and 15 were stored at 25° C. and a humidity of 75% for one week, and variations in thicknesses and hardness of the orally disintegrating tablets before and after storage were evaluated. Amounts of variations in the thicknesses and the hardness of the orally disintegrating tablets of Reference Example 5 and Comparative Examples 14 and 15 before and after storage are shown in FIG. 8.

From the result of FIG. 8, a significant increase in the thicknesses and a significant decrease in hardness due to storage under a high humidity condition were observed in the orally disintegrating tablets of Comparative Examples 14 and 15. On the other hand, in the orally disintegrating tablet of Reference Example 5, an increase in thickness and a decrease in hardness were significantly suppressed after storage as compared with the orally disintegrating tablets of Comparative Examples 14 and 15. As shown in FIG. 8, it was revealed that the orally disintegrating tablet of Reference Example 5 exhibited the hardness and the oral disintegration time equal to or more than those of the orally disintegrating tablets of Comparative Examples 14 and 15, and the orally disintegrating tablet of Reference Example 5 realized an orally disintegrating tablet which is also excellent in humidity resistance.

Example 1

As Example 1 of the present invention, an orally disintegrating tablet was produced by blending L-HPC and crospovidone in a ratio of 5:4. Dispersion liquid was prepared by dispersing 25 g of NBD-022 (Shin-Etsu Chemical Co., Ltd.) as the L-HPC into 745 ml of purified water. A mixture was obtained in a fluidized bed granulator (manufactured by POWREX CORP., Model: MP-01) by mixing 405 g of Mannit P (Mitsubishi Shoji Foodtech Co., Ltd.) as the D-mannitol, 10 g of Kollidon CL-F (BASF Corporation) and 10 g of Kollidon CL-M as the crospovidone, and 50 g of PH-101 (Asahi Kasei Corporation) as the microcrystalline cellulose. A fluidized bed granulation was performed while spraying the dispersion liquid to the obtained mixture. An additive for an orally disintegrating tablet of Example 1 was obtained by sizing the obtained granulated product with Sieve No. 22. Powder before tableted was obtained by mixing 5 g of magnesium stearate (Taihei Chemical Industrial Co., Ltd.) in the additive for an orally disintegrating tablet of Example 1. The orally disintegrating tablet of Example 1 was obtained by using a tableting machine (VELA5 manufactured by KIKUSUI SEISAKUSHO LTD.) to tablet the powder before tableted to obtain a tablet having a weight of 200 mg.

Example 2

As Example 2, an orally disintegrating tablet of Example 2 was produced in the same manner as Example 1, except that the granulation liquid was prepared by dispersing 10 g of Kollidon CL-F (BASF Corporation) and 10 g of Kollidon CL-M in purified water as the crospovidone and fluidized bed granulation was performed while spraying the granulation liquid to a mixture of L-HPC, D-mannitol and microcrystalline cellulose.

Example 3

As Example 3, an orally disintegrating tablet of Example 3 was produced in the same manner as Example 1, except that purified water was used as the granulation liquid and fluidized bed granulation was performed while spraying the purified water to a mixture of L-HPC, D-mannitol, crospovidone and microcrystalline cellulose.

Example 4

As Example 4, an orally disintegrating tablet of Example 4 was produced in the same manner as Example 1, except that the granulation liquid was prepared by dispersing 35 g of D-mannitol into purified water and fluidized bed granulation was performed while spraying the granulation liquid to a mixture of L-HPC, D-mannitol (370 g), crospovidone, and microcrystalline cellulose.

Example 5

As Example 5, an orally disintegrating tablet of Example 5 was produced in the same manner as Example 1, except that the granulation liquid was prepared by dispersing microcrystalline cellulose into purified water and fluidized bed granulation was performed while spraying the granulation liquid to a mixture of L-HPC, D-mannitol and crospovidone.

Comparative Example 18

As Comparative Example 18, an orally disintegrating tablet was produced by blending L-HPC and crospovidone in a ratio of 11:2. A mixture was obtained in a fluidized bed granulator (manufactured by POWREX CORP., Model: MP-01) by using purified water as the granulation liquid and mixing 55 g of L-HPC, 385 g of D-mannitol, 10 g of Kollidon CL-F (BASF Corporation) as the crospovidone, and 50 g of microcrystalline cellulose. An orally disintegrating tablet of Comparative Example 18 was produced in the same manner as Example 1, except that fluidized bed granulation was performed while spraying water to the obtained mixture.

Comparative Example 19

As Comparative Example 19, an orally disintegrating tablet of Comparative Example 19 was produced in the same manner as Comparative Example 18, except that the granulation liquid was prepared by dispersing a half of the amount of low-substituted hydroxypropyl cellulose to be added in purified water and fluidized bed granulation was performed while spraying the granulation liquid to a mixture of a half of the addition amount of low-substituted hydroxypropyl cellulose, D-mannitol, crospovidone, and microcrystalline cellulose.

Comparative Example 20

As Comparative Example 20, an orally disintegrating tablet of Comparative Example 20 was produced in the same manner as Comparative Example 18, except that the granulation liquid was prepared by dispersing microcrystalline cellulose into purified water and fluidized bed granulation was performed while spraying the granulation liquid to a mixture of low-substituted hydroxypropyl cellulose, D-mannitol and crospovidone.

Comparative Example 21

As Comparative Example 21, an orally disintegrating tablet of Comparative Example 21 was produced in the same manner as Comparative Example 18 except that the granulation liquid was prepared by dispersing a half amount of microcrystalline cellulose to be added into purified water and fluidized bed granulation was performed while spraying the granulation liquid to a mixture of low-substituted hydroxypropyl cellulose, D-mannitol, crospovidone, and a half of the addition amount of microcrystalline cellulose.

Comparative Example 22

As Comparative Example 22, an orally disintegrating tablet of Comparative Example 22 was produced in the same manner as Comparative Example 18, except that the granulation liquid was prepared by dispersing crospovidone into purified water and fluidized bed granulation was performed while spraying the granulation liquid to a mixture of low-substituted hydroxypropyl cellulose, D-mannitol and microcrystalline cellulose.

The orally disintegrating tablets of Examples 1 to 5 and Comparative Examples 18 to 22 were each produced using the tableting pressures of 6 kN, 9 kN and 12 kN, respectively.
(Hardness)

Regarding the orally disintegrating tablets of Examples 1 to 5 and Comparative Examples 18 to 22, the hardness of the tablet was measured using a tablet hardness tester (DC-50, OKADA SEIKO CO., LTD.) and an average value of the measured values of 3 tablets was calculated.
(Oral Disintegration Time)

Regarding the orally disintegrating tablets of Examples 1 to 5 and Comparative Examples 18 to 22, the oral disintegration time was measured by a sensory test.

Regarding the orally disintegrating tablets of Examples 1 to 5 and Comparative Examples 18 to 22 tableted using three tableting pressures, results of measurement of hardness and an oral disintegration time at the respective tableting pressures are shown in FIG. 9. The result of FIG. 9 revealed that the orally disintegrating tablets of Examples 1 to 5 having L-HPC and crospovidone blended in a ratio of 5:4 could obtain hardness corresponding to the tableting pressure, had excellent formability and could obtain quick disintegrability regardless of the additive contained in the granulation liquid.
(Evaluation of Humidity Resistance)

The orally disintegrating tablets of Examples 1 to 5 were produced adopting the tableting pressure of 9 kN. The orally disintegrating tablets of Examples 1 to 5 were stored at 25° C. and a humidity of 75% for one week, and variations in thickness and hardness of the orally disintegrating tablets of Examples 1 to 5 before and after the storage were evaluated. The amounts of variations in thickness and hardness of the orally disintegrating tablets of Examples 1 to 5 before and after the storage are shown in FIG. 10. From the result in FIG. 10, a significant difference in the influence on the humidity resistance due to the different additives used in the granulation liquids was not observed.
(Evaluation of Addition Preparation of Neusilin)

A preparation having Neusilin using the orally disintegrating tablet of Example 2 was evaluated.

Example 6

As Example 6, an orally disintegrating tablet of Example 6 containing 1% Neusilin was obtained by adding 3 g of Neusilin to 300 g of the additive for the orally disintegrating tablet of Example 2 and tableting the powder before tableting to obtain a tablet having a weight of 200 mg.

Example 7

As Example 7, an orally disintegrating tablet of Example 7 containing 3% Neusilin was obtained by adding 9 g of Neusilin to 300 g of the additive for the orally disintegrating tablet of Example 2 and tableting the powder before tableting to obtain a tablet having a weight of 200 mg.

Example 8

As Example 8, an orally disintegrating tablet of Example 8 containing 5% Neusilin was obtained by adding 15 g of Neusilin to 300 g of the additive for the orally disintegrating tablet of Example 2 and tableting the powder before tableting to obtain a tablet having a weight of 200 mg.

Example 9

As Example 9, an orally disintegrating tablet having L-HPC and crospovidone blended in a ratio of 5:4 was produced. A mixture was obtained by using purified water as the granulation liquid and mixing 15 g of Neusilin, 390 g of Mannit P (Mitsubishi Shoji Foodtech Co., Ltd.) as the D-mannitol, 25 g of NBD-022 (Shin-Etsu Chemical Co., Ltd.) as the L-HPC, 10 g of Kollidon CL-F (BASF Corporation) and 10 g of Kollidon CL-M as the crospovidone and 50 g of PH-101 (Asahi Kasei Corporation) as the microcrystalline cellulose in a fluidized bed granulator (manufactured by POWREX CORP., Model: MP-01). Fluidized bed granulation was performed while spraying the purified water to the obtained mixture. The obtained granulated product was sized with Sieve No. 22. Powder before tableting was obtained by mixing 5 g of magnesium stearate (Taihei Chemical Industrial Co., Ltd.) to the sized granules. An orally disintegrating tablet of Example 9 containing 3% Neusilin was obtained by using a tableting machine (VELA5 manufactured by KIKUSUI SEISAKUSHO LTD.) to tablet the powder before tableting to obtain a tablet having a weight of 200 mg.

Example 10

As Example 10, an orally disintegrating tablet having L-HPC and crospovidone blended in a ratio of 5:4 was produced. Dispersion liquid was prepared by dispersing 15 g of Neusilin into 350 ml of purified water. A mixture was obtained by mixing 405 g of Mannit P (Mitsubishi Shoji Foodtech Co., Ltd.) as the D-mannitol, 25 g of NBD-022 (Shin-Etsu Chemical Co., Ltd.) as the L-HPC, 10 g of Kollidon CL-F (BASF Corporation) and 10 g of Kollidon CL-M as the crospovidone, and 50 g of PH-101 (Asahi Kasei Corporation) as the microcrystalline cellulose in a fluidized bed granulator (manufactured by POWREX CORP., Model: MP-01). Fluidized bed granulation was performed while spraying the dispersion liquid to the obtained mixture. The obtained granulated product was sized with Sieve No. 22. Powder before tableting was obtained by mixing 5 g of magnesium stearate (Taihei Chemical Industrial Co., Ltd.) to the sized granules. An orally disintegrating tablet of Example 10 containing 3% Neusilin was obtained by using a tableting machine (VELA5 manufactured by KIKUSUI SEISAKUSHO LTD.) to tablet the powder before tableting to obtain a tablet having a weight of 200 mg.

Example 11

As Example 11, an orally disintegrating tablet having L-HPC and crospovidone blended in a ratio of 5:4 was produced. Dispersion liquid was prepared by dispersing 15 g Neusilin and 150 g of Mannit P (Mitsubishi Shoji Foodtech Co., Ltd.) as the D-mannitol into 350 ml of purified water. A mixture was obtained by mixing 240 g of D-mannitol, 25 g of NBD-022 (Shin-Etsu Chemical Co., Ltd.) as the L-HPC, 10 g of Kollidon CL-F (BASF Corporation) and 10 g of Kollidon CL-M as the crospovidone, and 50 g of PH-101 (Asahi Kasei Corporation) as the microcrystalline cellulose in a fluidized bed granulator (manufactured by POWREX CORP., Model: MP-01). Fluidized bed granulation was performed while spraying the dispersion liquid to the obtained mixture. The obtained granulated product was sized with Sieve No. 22. Powder before tableting was obtained by mixing 5 g of magnesium stearate (Taihei Chemical Industrial Co., Ltd.) to the sized granules. An orally disintegrating tablet of Example 11 containing 3% Neusilin was obtained by using a tableting machine (VELA5 manufactured by KIKUSUI SEISAKUSHO LTD.) to tablet the powder before tableting obtain a tablet having a weight of 200 mg.

Regarding the orally disintegrating tablets of Examples 2 and 6 to 11 tableted using three tableting pressures, results of measurement of hardness and an oral disintegration time at the respective tableting pressures are shown in FIG. 11. From the results in FIG. 11, it was revealed that the orally disintegrating tables of Examples 6 to 11 having L-HPC and crospovidone blended in a ratio of 5:4 could obtain high hardness and excellent formability as compared with the orally disintegrating tablet of Example 2, without slowing down the disintegration time, in the range of the effective addition amount of Neusilin regardless of the additive contained in the granulation liquid. Further, it was revealed that Examples 6 to 8 having Neusilin added after mixing could obtain particularly high hardness as compared with the orally disintegrating tablet of Example 2 not containing Neusilin.

(Evaluation of Humidity Resistance)

The orally disintegrating tablets of Examples 2 and 7 were produced using the tableting pressure of 9 kN. The orally disintegrating tablets of Examples 2 and 7 were stored at 25° C. and a humidity of 75% for one week, and variations in weight, thickness, hardness and oral disintegration time of the orally disintegrating tablets of Examples 2 and 7 before and after the storage were evaluated. The amounts of variations in the weight, thickness, hardness and oral disintegration time of the orally disintegrating tablets of Examples 2 and 7 before and after the storage are shown in FIG. 12. From the results in FIG. 12, an increase in weight and swelling of the thickness were suppressed by adding Neusilin, and a favorable impact on humidity resistance was observed.

According to one embodiment of the present invention, there is provided a novel additive for an orally disintegrating tablet providing quick disintegrability and tablet hardness to an orally disintegrating tablet, and a producing method therefor.

What is claimed is:

1. An additive granule for an orally disintegrating tablet consisting of:
    D-mannitol;
    low-substituted hydroxypropyl cellulose;
    crospovidone; and
    microcrystalline cellulose,
    wherein
    the low-substituted hydroxypropyl cellulose is selected from the group consisting of:
    low-substituted hydroxypropyl cellulose having a mean particle size of 45 µm, a 90% cumulated particle size of 135 µm, and a substitution degree of hydroxypropoxy groups of 11%;
    low-substituted hydroxypropyl cellulose having a mean particle size of 55 µm, a 90% cumulated particle size of 125 µm, and a substitution degree of hydroxypropoxy groups of 11%; and
    low-substituted hydroxypropyl cellulose having a mean particle size of 45 µm, a 90% cumulated particle size of 100 µm, and a substitution degree of hydroxypropoxy groups of 8%,
    the low-substituted hydroxypropyl cellulose and the crospovidone are included in in a ratio of 5:4, and
    the crospovidone has a mean particle size of 50 µm or less.

2. The additive granule for an orally disintegrating tablet according to claim 1, wherein the D-mannitol has a mean particle size of 50 µm or less.

3. The additive granule for an orally disintegrating tablet according to claim 1, wherein the microcrystalline cellulose has a bulk density of 0.22 g/cm$^3$ or more.

4. The additive granule for an orally disintegrating tablet according to claim 2, wherein the microcrystalline cellulose has a bulk density of 0.22 g/cm$^3$ or more.

5. An orally disintegrating tablet comprising:
    the additive granule for an orally disintegrating tablet according to claim 1; and
    a pharmaceutical active ingredient.

6. A method of producing an additive granule for an orally disintegrating tablet according to claim 1, comprising:
    preparing a granulation liquid of water, or a granulation liquid of a dispersion by dispersing in water at least one additive selected from the group consisting of low-substituted hydroxypropyl cellulose, D-mannitol, crospovidone, and microcrystalline cellulose; and performing granulation while spraying the granulation liquid to a mixture consisting of all the additives excluding the additive contained in the granulation liquid, wherein the low-substituted hydroxypropyl cellulose is selected from the group consisting of:

low-substituted hydroxypropyl cellulose having a mean particle size of 45 μm, a 90% cumulated particle size of 135 μm, and a substitution degree of hydroxypropoxy groups of 11%;

low-substituted hydroxypropyl cellulose having a mean particle size of 55 μm, a 90% cumulated particle size of 125 μm, and a substitution degree of hydroxypropoxy groups of 11%; and low-substituted hydroxypropyl cellulose having a mean particle size of 45 μm, a 90% cumulated particle size of 100 μm, and a substitution degree of hydroxypropoxy groups of 8%, the low-substituted hydroxypropyl cellulose and the crospovidone are included in a ratio of 5:4, and the crospovidone has a mean particle size of 50 μm or less.

7. The producing method according to claim 6, wherein the D-mannitol has a mean particle size of 50 μm or less.

8. The producing method according to claim 6, wherein the microcrystalline cellulose has a bulk density of 0.22 g/cm$^3$ or more.

* * * * *